US011177102B2

(12) United States Patent
Jouper

(10) Patent No.: US 11,177,102 B2
(45) Date of Patent: Nov. 16, 2021

(54) VOLATILE ORGANIC COMPOUND CONTROLLED RELAY FOR POWER APPLICATIONS

(71) Applicant: Astronics Advanced Electronic Systems Corp., Kirkland, WA (US)

(72) Inventor: Jeffrey A. Jouper, Newcastle, WA (US)

(73) Assignee: Astronics Advanced Electronic Systems Corp., Kirkland, WA (US)

( * ) Notice: Subject to any disclaimer, the term of this patent is extended or adjusted under 35 U.S.C. 154(b) by 0 days.

(21) Appl. No.: 15/956,048

(22) Filed: Apr. 18, 2018

(65) Prior Publication Data

US 2018/0323026 A1 Nov. 8, 2018

Related U.S. Application Data

(60) Provisional application No. 62/501,842, filed on May 5, 2017.

(51) Int. Cl.
*H01H 47/22* (2006.01)
*B64D 45/00* (2006.01)
*H04B 7/14* (2006.01)

(52) U.S. Cl.
CPC .............. *H01H 47/22* (2013.01); *B64D 45/00* (2013.01); *B64D 2045/009* (2013.01); *B64D 2221/00* (2013.01); *H04B 7/14* (2013.01)

(58) Field of Classification Search
CPC ........ H01H 47/22; H01H 47/24; H01H 47/20; F23N 5/08; H04B 7/14; G01N 33/00;
(Continued)

(56) References Cited

U.S. PATENT DOCUMENTS

| 5,445,795 A | 8/1995 | Lancaster et al. |
| 9,600,998 B2 * | 3/2017 | Mumey .................. G08B 21/14 |

(Continued)

FOREIGN PATENT DOCUMENTS

| CN | 205141628 U | 4/2016 |
| CN | 106104966 A | 11/2016 |

(Continued)

OTHER PUBLICATIONS

PCT/US 18/30344, Search Report, dated Jul. 20, 2018.
(Continued)

*Primary Examiner* — Rexford N Barnie
*Assistant Examiner* — Terrence R Willoughby
(74) *Attorney, Agent, or Firm* — Wiggian and Dana LLP; Gregory S. Rosenblatt; Thomas M. Landman

(57) ABSTRACT

A power relay is controlled by the presence of Volatile Organic Compounds that are often emitted by outgassing from electronic components during overheat and failure conditions. The relay housing contains a standard power relay of single pole single throw (SPST) or a multi-pole double throw relay depending on the application. A micro VOC integrated circuit is placed within the housing allowing access to ambient air through ports in the side of the relay. Air quality is sampled periodically or continuously as is required by the system to adequately monitor for fault events and, in the event of a fault, latch the relay mechanism OPEN breaking the flow of electrical energy the circuit downstream.

17 Claims, 3 Drawing Sheets

(58) Field of Classification Search
CPC .......... G01N 33/0031; G01N 33/0047; G01N 33/0062; G01N 33/004; G01N 27/12; G01N 27/127; G01N 27/128; H04L 1/00; H04L 1/0041; H04L 63/0428
USPC ................ 307/116, 66, 64, 9.1, 10.1, 80, 17
See application file for complete search history.

(56) References Cited

U.S. PATENT DOCUMENTS

| | | |
|---|---|---|
| 2004/0140191 A1 | 7/2004 | Jerg et al. |
| 2004/0160329 A1 | 8/2004 | Flanc |
| 2004/0218330 A1 | 11/2004 | Natili et al. |
| 2007/0099137 A1* | 5/2007 | Donnelly ................ F23N 5/003 431/79 |
| 2007/0120693 A1 | 5/2007 | Vij |
| 2008/0182215 A1* | 7/2008 | Sid ..................... G01N 33/0063 431/18 |
| 2011/0276183 A1 | 11/2011 | Liu |
| 2013/0153798 A1* | 6/2013 | Kucera ................... F23N 1/002 251/129.01 |
| 2015/0138729 A1* | 5/2015 | Desai ................ H05K 7/20272 361/699 |
| 2015/0276693 A1* | 10/2015 | Sid ........................ B60K 28/10 307/116 |
| 2016/0019769 A1* | 1/2016 | Mumey .................. G08B 21/14 340/632 |
| 2016/0063833 A1 | 3/2016 | Schultz et al. |
| 2016/0231721 A1* | 8/2016 | Lakshmanan .......... H01H 71/00 |
| 2016/0351040 A1* | 12/2016 | Zokaei .................... H04W 4/12 |
| 2016/0358722 A1* | 12/2016 | Lakshmanan ............ H01H 9/54 |
| 2017/0241964 A1* | 8/2017 | Vereecken ........... G01N 33/004 |
| 2018/0356357 A1* | 12/2018 | Samarao ............... G01N 27/127 |
| 2018/0373304 A1* | 12/2018 | Davis ....................... H01H 9/56 |

FOREIGN PATENT DOCUMENTS

| | | |
|---|---|---|
| CN | 106442030 A | 2/2017 |
| JP | H0896280 A | 4/1996 |
| JP | 2009257641 A | 11/2009 |
| JP | 2016054074 A | 4/2016 |
| JP | 2016091803 A | 5/2016 |
| WO | 2004074809 A2 | 9/2004 |

OTHER PUBLICATIONS

PCT/US2018/030344, International Preliminary Report on Patentability, dated Nov. 5, 2019.
China Patent Office, First Office Action and Search Report for CN 201880029364, dated Jan. 6, 2021.

* cited by examiner

VOLATILE ORGANIC COMPOUND CONTROLLED RELAY FOR POWER APPLICATIONS

CROSS-REFERENCE TO RELATED PATENT APPLICATION

This patent application claims a benefit to U.S. Provisional Patent Application Ser. No. 62/501,842, titled "Volatile Organic Compound Controlled Relay for Power Applications," that was filed on May 5, 2017. The disclosure of U.S. 62/501,842 is incorporated by reference herein in its entirety.

BACKGROUND OF THE DISCLOSURE

Fuses are often counted upon for extinguishing fires within a housing based on the circuit producing a short circuit or overload that will eventually clear the fuse. Other mechanisms such as thermal fuses and thermal switches have also been used with limited results as the point of thermal stress must be mechanically connected to the thermally overstressed component in order to perform its intended function. Many smaller events and transient events may cause smoke but not be of adequate magnitude to trip either a thermal limit or an input fuse. This leaves a wounded or failing product in operation until such time as the unit fully fails, many time causing additional stress on personnel within a small area, such as a passenger cabin of an aircraft, of the failing device.

SUMMARY OF THE DISCLOSURE

Disclosed herein is a volatile organic compound (VOC) controlled relay that is utilized as a switching relay to enable and disable power to electronic circuits. This VOC controlled relay is particularly suited to power conversion electronics where high power and manipulation of high power or voltage carries risks of failures due to overstress, unforeseen input variations, thermal overstress, component failures, poor design practices and other failure mechanisms.

It is a feature of the VOC controlled relay that miniaturization and microelectronics enable integration of a sensor, microcontroller and power relay in an integrated package to become a single sensing and power control device.

DETAILED DESCRIPTION

Figure 1:
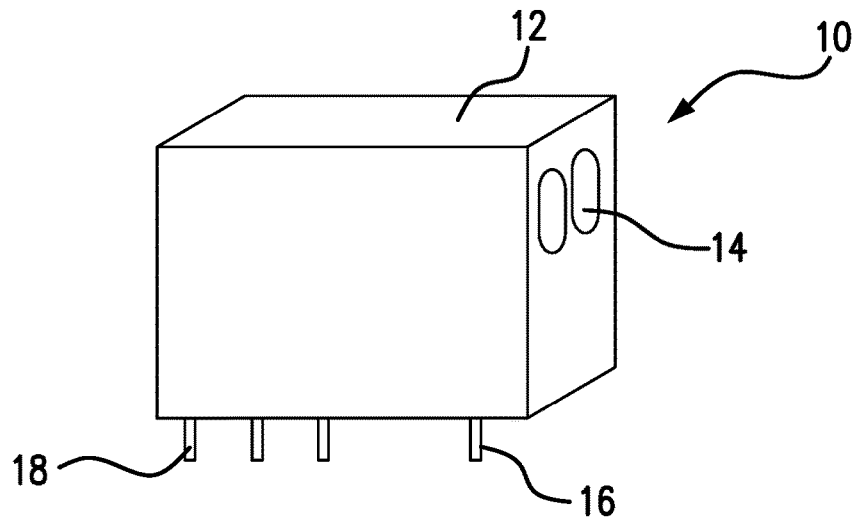
FIG. 1 is an isometric view of a VOC controlled relay as described herein.

FIG. 1 is an isometric view of a VOC controlled relay 10 having a housing 12 and gas ports 14. A plurality of leads provide electrical interconnect between the VOC controlled relay and external circuitry. These leads include controller leads 16 and relay leads 18.

Figure 2:
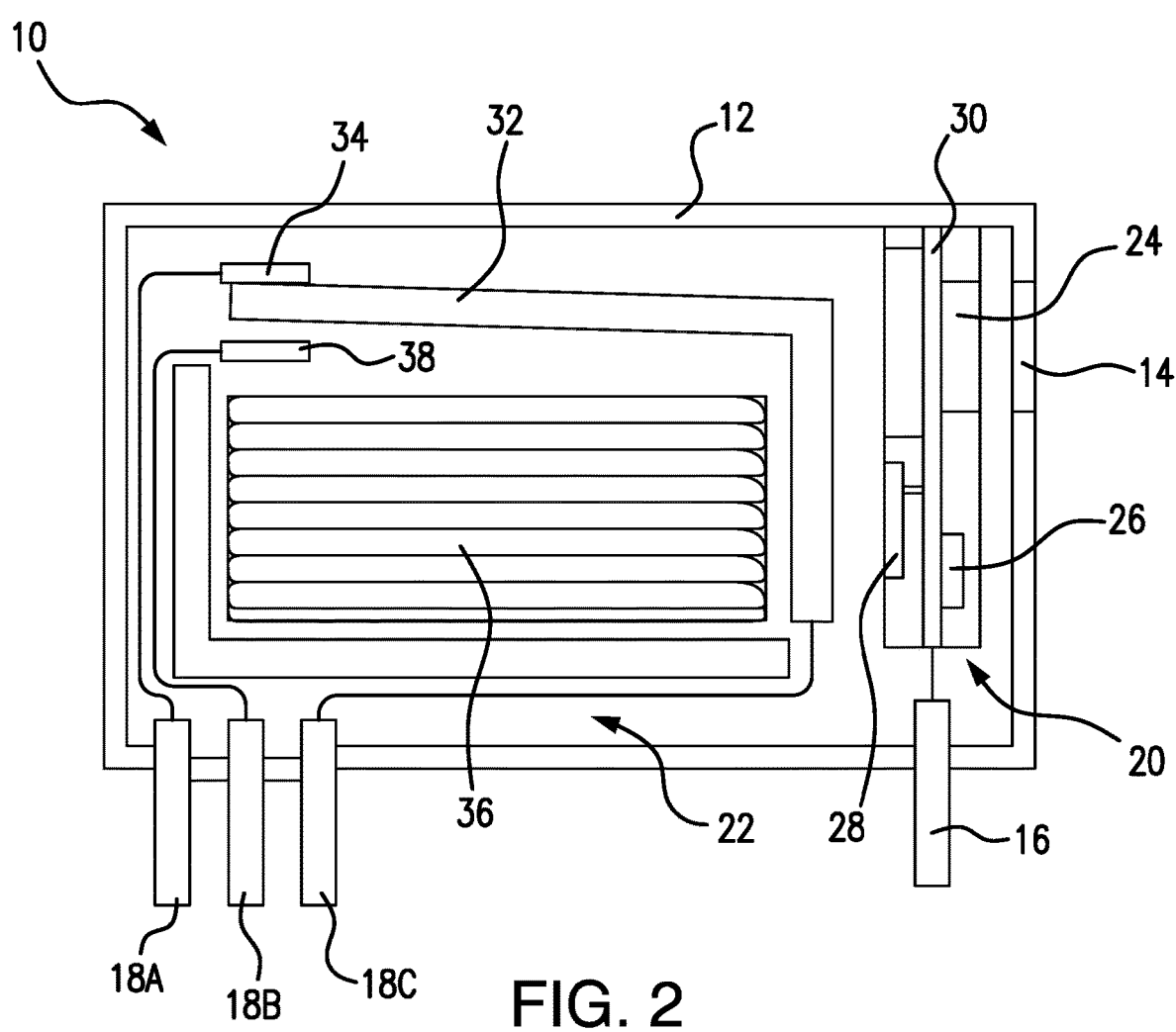
FIG. 2 is a cross-sectional view of the VOC controlled relay.

FIG. 2 is a cross-sectional view of the VOC controlled relay 10. Contained within housing 12 are a controller portion 20 and a relay portion 22. The controller portion 20 includes a gas sensor 24 and a microcontroller 26. Optionally, radio 28 may be included. Data and power is provided through bus 30 that is electrically interconnected to controller lead 16. The gas sensor 24 and microcontroller 26 can either be powered from the power input to the relay portion 22 or from a secondary circuit separate from the relay assembly. A self-contained power relay portion 22 with separate power supply to power the gas sensor 24 and the microcontroller 26 is one preferred embodiment.

The gas sensor 24 receives a gaseous input through gas port 14 and measures a level of VOC. The gaseous input is typically ambient air. The sampling may be continuous or periodic as required by the system to adequately monitor for fault events. The VOC level is communicated with the microcontroller 26 to monitor the VOC level. Dependent on the concentration of VOC and the rate of change of VOC concentration, the microcontroller sends the data over the optional radio 28 to an external monitor. If a programmed threshold level is exceeded, the microcontroller 26 opens the relay 32 removing power from the unit under supervision. As one example, the microcontroller may instruct the relay to open when the VOC concentration exceeds a nominal level based on the environment by a predetermined amount, such as by 50%, by concentration. The nominal level may be determined by taking several measurements over time to establish a baseline. An elevated VOC concentration is an indication that there is overheating or outgassing of components. Opening the relay causes power to be removed from the device under supervision. As an example, if the baseline VOC concentration is 480 parts per billion (ppb) and when a reading is taken the concentration increased to over 700 ppb, the relay would be actuated to remove power.

VOC gases enter through the gas ports 14 extending through housing 12 where they are analyzed for content of materials. This information is processed by the microcontroller 26 which compares the gross value of VOC particles to the maximum value allowed based on a programmed value. The programmed value could include an offset for other environmental contaminates such as dust or other organic compounds to ensure no false triggers of the system occur. Setting of the trip value could be done at the factory or with the use of the optional radio 28. This value could be set on location for the device it is monitoring. The radio would report the continuously or periodically monitored value of the VOC level. One suitable gas sensor is a micro VOC integrated circuit, such as the ultra-low power digital gas sensor for monitoring indoor air quality sold by AMS USA Inc. (Cupertino, Calif.) as the CCS811 Gas Sensor Solution.

Relay 32 is normally in the closed position, in electrical contact with a first contactor 34, so that first relay lead 18A and third relay lead 18C are electrically interconnected and the device controlled by the VOC controlled relay 10 functions normally. When a threshold level of VOC is exceeded, magnetic coil 36 is powered causing the relay 32 to break contact with the first contactor 34 and make contact with the second contactor 38. When the relay 32 is in electrical contact with the second contactor 38, second relay lead 18B and third relay lead 18C are electrically interconnected and the device controlled by the VOC controlled relay 10 does not receive power.

The relay 32 may be a single pole single throw (SPST) relay or a multi-pole double throw relay depending on the application.

Once the microcontroller 26 determines that the VOC level exceeds the programmed level, the microcontroller 26 signals to the relay portion to "set" the relay 32 latching it OPEN. This removes power from unit under supervision. To reset the latching relay 32, either an additional electrical signal or a mechanical push button may be used to move the relay 32 back to the normally closed position, in electrical contact with first contactor 34.

While FIGS. 1 and 2 illustrate the gas sensor 22 contained within the same housing 12 as the relay 22, alternatively, the gas sensor may be contained in a separate housing and be located remotely from the relay. Communication between the gas sensor and the relay would then be by any suitable wired or wireless communication system.

Figure 3:
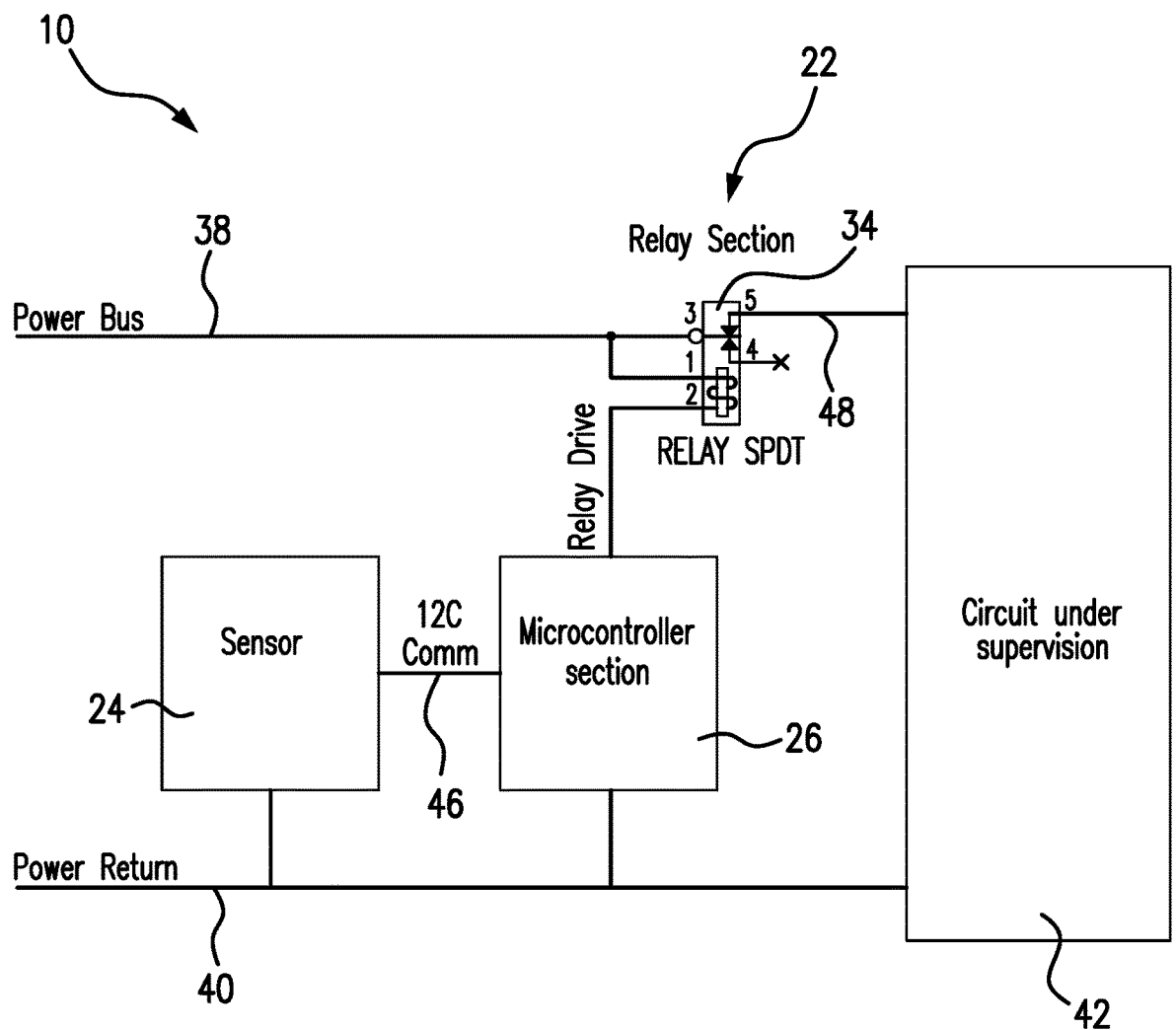
FIG. 3 is a block diagram of the VOC controlled relay.

FIG. 3 is a block diagram depiction of one embodiment. Power is supplied via the power bus 38 and power return 40 lines. The power may be AC or DC power depending on application. For an exemplary passenger cabin of an aircraft application, the power is typically 115 volts AC at 400 Hz. Minor adjustments to the circuit could be required depending on the power bus source of choice. Power is fed through the normally closed first contactor 34 of the relay portion 22 to the device under supervision 42 through the power output 48 of the relay portion 22. The VOC sensor (Gas Sensor 24) continuously monitors the air quality within the unit under supervision 42. The VOC content is requested by the microcontroller 26 through an Inter-Integrated Circuit (I2C) interface 46. When a measurement is complete, the VOC sensor 24 responds over the I2C interface 46 to the microcontroller 26 with the VOC content. The microcontroller 26 determines if the value of the response is greater than the programmed limit. The programmed limit can be set at the factory or loaded through a wireless interface to the microcontroller 26 through a radio. Microcontrollers 26 with integrated radios are a design method that keeps the device 10 as small as possible.

Figure 4:
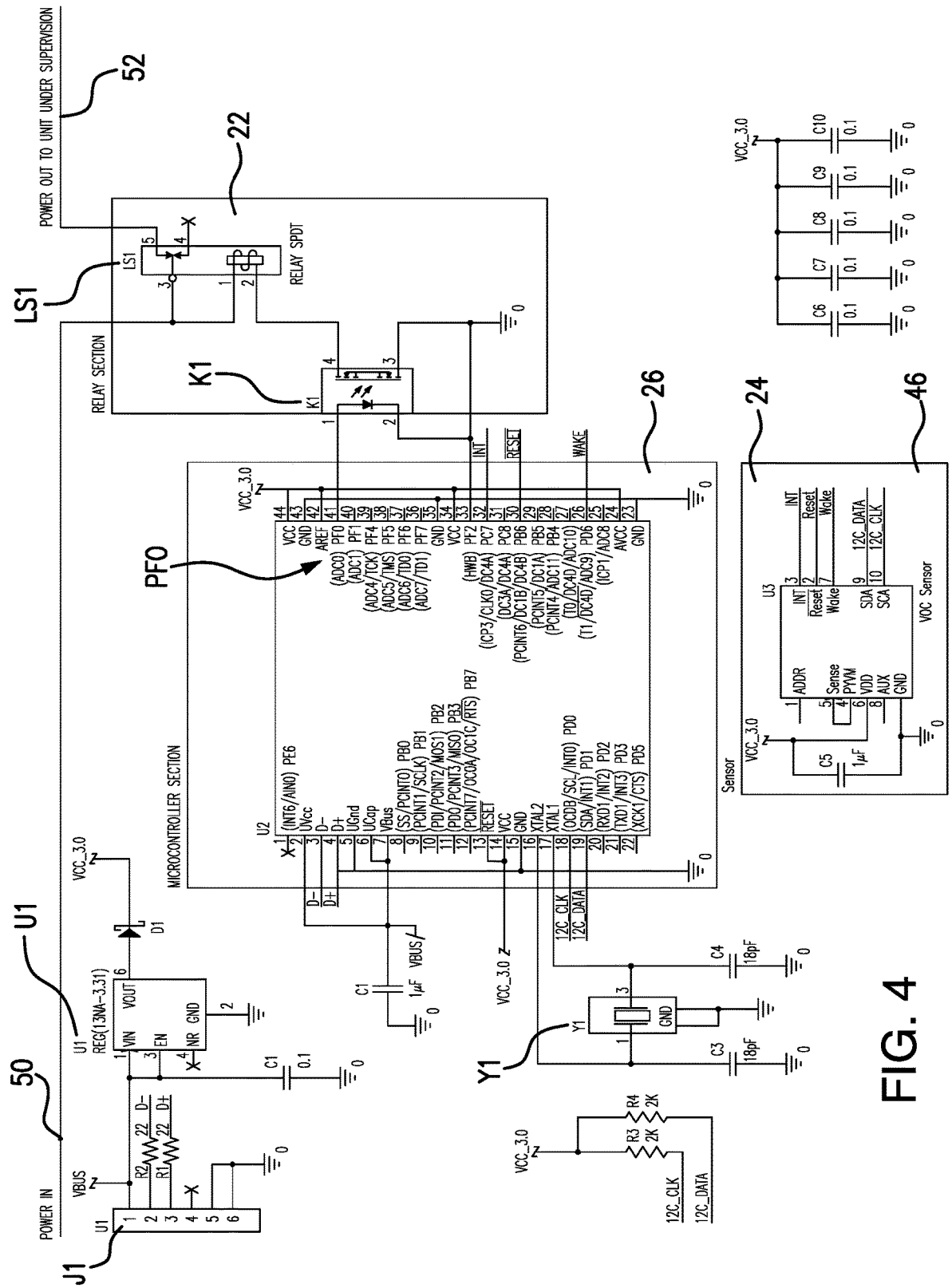
FIG. 4 is a schematic of the VOC controlled relay.

FIG. 4 schematically depicts electrical connections from component to component. The I2C interface 46 between the microcontroller 26 and the sensor 24 allows for bidirectional communication between these devices. Power for the microcontroller and sensor is derived from an appropriate power supply taken from the input power. The method of this is determined by the input power bus 50 voltage and form chosen.

J1 of FIG. 4 is a programming port to allow firmware to load into microcontroller (26) U2. U1 is a voltage regulator to convert the 5 VDC of the Universal Serial Bus (USB) interface to a regulated 3.0 VDC used by the microcontroller for operation during programming. Y1 is a crystal oscillator to set the operating frequency of the microcontroller instruction cycle timing to operably execute the firmware instructions. The firmware loaded is operable to monitor the VOC sensor 24 through the inter integrated circuit (I2C) interface 46. The microcontroller 26 contains non-volatile memory for storing the firmware as well as the nominal value of the VOC sensor under nominal operating conditions for comparison to operational readings taken.

When the microcontroller receives a reading from the VOC sensor 46 showing a dramatic increase in VOC value, the microcontroller determines that a smoke, heating or outgassing event is occurring. The microcontroller though port PF0 sets the port to a logic 1 enabling relay control K1. K1 in turn drive relay (22) LS1 to the open state removing power 52 to the unit under supervision. Driving the relay ON only during a fault decreases the power consumption of this circuit. Either drive ON, OFF or the use of a latching state relay may be effected by minor modifications of the circuit.

Power to the microcontroller 26 during operation is taken from the POWER IN 50. Converting power from the POWER IN form is required to produce a 3.0 VDC bias supply to operate the microcontroller 26 and VOC sensor 24 as well as the relay drive circuit K1. Power conversion from line voltage or DC voltage is well known in the industry and is not included in this disclosure.

I claim:

1. A switching relay to enable and disable electric power to an electronic circuit, the switching relay comprising:
   a gas sensor that measures a gas concentration in an ambient air environment and outputs a measured level of the gas concentration;
   a relay that is in a closed position when not energized and an open position when energized;
   a relay controller that controls the relay to open and close;
   a microcontroller in communication with the gas sensor and the relay controller; and
   a baseline gas concentration level that is calculated by the microprocessor from a plurality of measured gas concentration values received from the gas sensor over a predefined time duration and from an offset in accordance with environmental conditions;
   wherein the microcontroller is programmed to monitor measured gas concentration levels received from the gas sensor and compare said levels to the baseline level, and to control the relay controller to energize the relay when the measured gas concentration level exceeds the baseline level, thereby isolating the electronic circuit from a power source.

2. The switching relay of claim 1 wherein the gas sensor detects a concentration of a volatile organic compound (VOC).

3. The switching relay of claim 2 wherein the gas sensor is in gaseous communication with ambient air.

4. The switching relay of claim 3 wherein the gas sensor is programmed to continuously monitor the ambient air.

5. The switching relay of claim 3 wherein the gas sensor is programmed to periodically monitor the ambient air.

6. The switching relay of claim 3 wherein the microcontroller has a programmed limit of VOC stored in the nonvolatile memory.

7. The switching relay of claim 6 wherein the microcontroller is programmed to control the relay controller to energize the relay when the programmed limit of VOC is exceeded.

8. The switching relay of claim 7 wherein the microcontroller has an electrical interconnection to the relay controller and digitally communicates with the relay controller via the electrical interconnection.

9. The switching relay of claim 7 further including a radio in communication with the microcontroller.

10. The switching relay of claim 3 wherein the relay includes a magnetic coil that when energized opens isolating the electronic circuit from the power source.

11. The switching relay of claim 10 wherein the ambient air is from a passenger cabin of an aircraft.

12. The method of claim 11 wherein said monitoring of said ambient air is continuous.

13. The method of claim 11 wherein said monitoring of said ambient air is periodic.

14. The method of claim 11 wherein the predetermined threshold is stored in a nonvolatile memory of a microcontroller.

15. The method of claim 14 wherein the microcontroller communicates with the relay via a relay controller.

16. The method of claim 14 wherein the microcontroller communicates with a radio by an electrical interconnection.

17. A method to electrically isolate an electronic circuit from a power source when a volatile organic compound (VOC) level exceeds a predetermined threshold, comprising the steps of:

providing a switching relay having a VOC gas sensor, a relay that is in a closed position when not energized and an open position when energized, a relay controller that controls the switching relay to open and close, and a microcontroller in communication with both the VOC sensor and the relay;

calculating a baseline gas concentration level from a plurality of measured gas concentration values received from the VOC sensor over a predefined time duration and from an offset in accordance with environmental conditions;

storing the baseline value in a non-volatile memory;

monitoring ambient air; and causing the microcontroller to control the relay controller to energize the relay when the VOC level of the ambient air exceeds the baseline value opening the relay and isolating the electronic circuit.

* * * * *